(12) United States Patent
Takalo et al.

(10) Patent No.: US 7,018,851 B2
(45) Date of Patent: Mar. 28, 2006

(54) BIOSPECIFIC BINDING REACTANTS LABELED WITH NEW LUMINESCENT LANTHANIDE CHELATES AND THEIR USE

(75) Inventors: Harri Takalo, Turku (FI); Jaana Rosenberg, Turku (FI)

(73) Assignee: Innotrac Diagnostics Oy, Turku (FI)

( * ) Notice: Subject to any disclaimer, the term of this patent is extended or adjusted under 35 U.S.C. 154(b) by 449 days.

(21) Appl. No.: 10/365,637

(22) Filed: Feb. 13, 2003

(65) Prior Publication Data

US 2004/0166585 A1    Aug. 26, 2004

(51) Int. Cl.
G01N 33/533    (2006.01)
C12Q 1/68      (2006.01)
C07K 17/01     (2006.01)
C07F 5/00      (2006.01)

(52) U.S. Cl. .................. 436/546; 435/6; 530/391.3; 530/391.5; 530/405; 530/409; 534/15

(58) Field of Classification Search ............... 436/546; 435/6; 534/15; 530/405, 391.3, 391.5, 409; 546/256

See application file for complete search history.

(56) References Cited

U.S. PATENT DOCUMENTS

| | | | |
|---|---|---|---|
| 4,670,572 A | 6/1987 | Hinshaw et al. | 556/1 |
| 4,761,481 A | 8/1988 | Hale et al. | 546/296 |
| 4,772,563 A | 9/1988 | Evangelista et al. | 436/518 |
| 4,794,191 A | 12/1988 | Hinshaw et al. | 549/211 |
| 4,801,722 A | 1/1989 | Hinshaw et al. | 549/211 |
| 4,859,777 A | 8/1989 | Toner | 546/256 |
| 4,920,195 A | 4/1990 | Kankare et al. | 534/16 |
| 4,927,923 A | 5/1990 | Mathis et al. | 540/456 |
| 5,032,677 A | 7/1991 | Hale et al. | 530/402 |
| 5,055,578 A | 10/1991 | Hale et al. | 544/209 |
| 5,202,423 A | 4/1993 | Kankare et al. | 530/391.5 |
| 5,216,134 A | 6/1993 | Mukkala et al. | 534/15 |
| 5,324,825 A | 6/1994 | Kankare et al. | 534/16 |
| 5,571,897 A | 11/1996 | Takalo et al. | 534/15 |
| 5,859,215 A | 1/1999 | Rodriguez-Ubis et al. | 534/16 |

FOREIGN PATENT DOCUMENTS

| | | |
|---|---|---|
| EP | 0 493 745 | 7/1992 |
| EP | 0 369 000 | 4/1999 |
| WO | WO 93/5049 | 3/1993 |

OTHER PUBLICATIONS

Latva et al., 75 *J. Luminescence* 149 (1997).
Takalo et al., 79 *Helv. Chim. Acta* (1996).

*Primary Examiner*—Mary E. Ceperley
(74) *Attorney, Agent, or Firm*—James C. Lydon

(57) ABSTRACT

This invention relates to a luminescent lanthanide chelate comprising a lanthanide ion and a chelating ligand of formula (I)

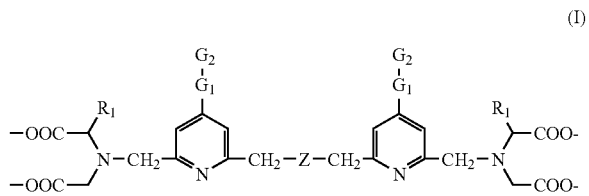

wherein $R_1$ is selected from the group consisting H, —COOH, —COO$^-$, —CH$_2$COOH and —CH$_2$COO$^-$; $G_1$ is a group consisting of one or two moieties each moiety being selected from the group consisting of ethynediyl, ethenylene, phenylene, biphenylene, naphthylene, pyridylene, pyrazinylene, pyrimidinylene, pyridazinylene, furylene, thienylene, pyrrolylene, imidazolylene, pyrazolylene, thiazolylene, isothiazolylene, oxazolylene, isoxazolylene, fyrazanylene, 1,2,4-triazol-3,5-ylene and oxadiazolylene; $G_2$ for coupling to a biospecific binding reactant is selected from the group consisting of amino, aminooxy, carbonyl, aldehyde or mercapto groups and activated forms made of them; Z is selected from the group consisting of carboxyalkyl amine, ether, thioether, carbonyl and unsubstituted or substitute methyl (—CR$_2$—) wherein group $R_2$ is selected from the group consisting of H, methyl, ethyl and carboxyalkyl; and the lanthanide ion is europium(III), terbium(III), dysprosiym (III) or samarium(III). This invention further relates to a detectable molecule comprising the lanthanide chelate and the use of the molecule in a method of carrying out a biospecific binding assay.

9 Claims, 1 Drawing Sheet

BIOSPECIFIC BINDING REACTANTS LABELED WITH NEW LUMINESCENT LANTHANIDE CHELATES AND THEIR USE

FIELD OF THE INVENTION

The present invention relates to detectable molecules comprising lanthanide chelates attached to a biospecific binding reactant and use of said detectable molecules in bioaffinity based binding assays. The invention further relates to new luminescent lanthanide chelates useful in the preparation of said detectable molecules.

BACKGROUND OF THE INVENTION

The publications and other materials used herein to illuminate the background of the invention, and in particular, cases to provide additional details respecting the practice, are incorporated by reference.

In specific binding assays, such as, e.g. immunoassays, DNA hybridization assays, receptor-binding assays, and cellular binding assays, generally the analytes to be measured are present at very low concentrations. Therefore, various labeling compounds have been developed that allow the labeling reactant to be detected and quantified at high sensitivity. In immunoassays and DNA hybridization assays time-resolved luminescence spectroscopy using lanthanide chelates is well known (e.g. I. Hemmilä, T. Stålberg, and P. Mottram (eds.), "Bioanalytical Applications of Labelling Technologies", Wallac, Turku, 1994 and D. Wild (eds), "The Immunoassay Handbook", Nature Publishing Group, 2001). Stable photoluminescent (referred in the context of this specification simply as luminescent) lanthanide chelates also have other applications, e.g. fluorescence microscopy and cytometry. Therefore, a number of attempts have been made to develop new highly luminescent chelates suitable for those types of time-resolved fluorometric applications. These include e.g. stable chelates composed of derivatives of pyridine (U.S. Pat. No. 4,920,195; U.S. Pat. No. 4,801,77; U.S. Pat. No. 4,761,481; U.S. Pat. No. 5,571,897; U.S. Pat. No. 5,859,215; Latva, M., Takalo, H., Mukkala, V. M., Matachescu, C., Rodriquez-Ubis, J. C. and Kankare, J., 1997, J. Luminescence, 75, 149; Takalo, H., Hemmilä, I., Sutela, T. and Latva, M., 1996, Helv. Chim. Acta, 79, 789), bipyridines (U.S. Pat. No. 5,216,134), terpyridines (U.S. Pat. No. 4,859,777, U.S. Pat. No. 5,202,423, U.S. Pat. No. 5,324,825) or various phenolic compounds (U.S. Pat. No. 4,670,572, U.S. Pat. No. 4,794,191, IT 42508A/89) as energy mediating groups and polycarboxylic acids as chelating parts. In addition, various dicarboxylate derivatives (U.S. Pat. No. 5,032,677, U.S. Pat. No. 5,055,578, U.S. Pat. No. 4,772,563), macrocyclic cryptates (U.S. Pat. No. 4,927,923, PCT WO 93/5049, EP 0 493 745), calixarenes (Sato, N. and Shinkai, S., 1993, J. Chem. Soc. Perkin Trans. 2, 621; Steemers, F. J., Verboom, W., Reinboudt, D. N., van der Tol, E. B. and Verhoeven, J. W., 1995, J. Am. Chem. Soc., 117, 9408), DTPA carbostril 124 conjugate (Selvin, P. R., Rana, T. M. and Hearst, J. E., 1994, J. Am. Chem. Soc., 116, 6029) and macrocyclic Schiff bases (EP 0 369 000) have been disclosed in patent applications and/or patents.

It is known that the luminescence lanthanide chelates are quenched in an aqueous solution. When water molecules are coordinated in the inner sphere of chelates, quenching is a result of an efficient, radiationless decay process involving vibronic coupling of lanthanide excited state and OH oscillation. The process is additive in regard to the number of OH oscillators, and hence the luminescence decay is inversely related to the number of bound water molecules. Various systems have been developed to avoid this phenomenon, such as using detergents and synergistic compounds, using high concentration of fluorine ions, removing water by drying prior to measurement, using a polymetric matrix, or measuring the luminescence in an organic solvent or in deuterium oxide. An ideal way to avoid direct aqueous quenching is to use stable, preferable nine dentate chelating agents, which do not allow the coordination of water with the chelated ion. In the above-mentioned chelates the lanthanide ion is normally coordinated to 7, 8 or 9 heteroatoms forming a seven-, eight- or nine-dentate chelate, respectively. Seven- and eight-dentate chelates contain from two to one water molecules and thus suffer aqueous quenching. It's generally assumed, that additional coordination atoms in nine—dentate chelates—having no water molecule in the first coordination sphere—don't have any additional positive effect in relation to aqueous quenching.

During an energy transfer process from an excited ligand to a lanthanide ion the energy undergoes intersystem crossing to one of ligand triplet states. The next step is a spin-forbidden transition of the energy, causing ligand phosphorescence, or an intra-molecular energy transfer to the lanthanide ion. Thermal decay, such as e.g. molecule thermal movement and rotation, is a known non-radiative deactivation process of mentioned triplet state. The lanthanide label chelates normally contains one reactive functional group for coupling the label to a biospecific binding reactant. Thus, in a labeled biomolecule the label may rotate and non-radiative deactivation of ligand triplet state is a possible phenomenon.

The general view is that several reactive binding groups in a label molecule cause cross reaction and formation of the biospecific binding reactant aggregates during the labeling process, and thus produce purification problems and decreased yield of labeled material.

SUMMARY OF THE INVENTION

An object of this invention is to provide an improved luminescent lanthanide chelate comprising a lanthanide ion and a chelating ligand.

Another object of the present invention is to provide an improved detectable molecule comprising a biospecific binding reactant attached to the luminescent lanthanide chelate.

Yet another object of this invention is to provide an improved labeling method of a biospecific binging reactant by using the luminescent lanthanide chelate label.

Thus according to one aspect this invention provides a luminescent lanthanide chelate comprising a lanthanide ion and a chelating ligand of the formula (I)

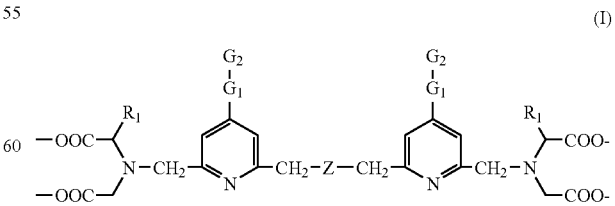

wherein,
a) $R_1$ is selected from the group consisting of H, —COOH, —COO⁻, —CH$_2$COOH and —CH$_2$COO⁻;

b) $G_1$ is a group consisting of one or two moieties each moiety being selected from the group consisting of ethynediyl (—C≡C—), ethenylene (—CH═CH—), phenylene, biphenylene, naphthylene, pyridylene, pyrazinylene, pyrimidinylene, pyridazinylene, furylene, thienylene, pyrrolylene, imidazolylene, pyrazolylene, thiazolylene, isothiazolylene, oxazolylene, isoxazolylene, fyrazanylene, 1,2,4-triazol-3,5-ylene and oxadiazolylene;

c) $G_2$ for coupling to a biospecific binding reactant is selected from the group containing amino, aminooxy, carbonyl, aldehyde or mercapto groups or an activated form made of them;

d) Z is selected from the group consisting of carboxyalkyl amine, ether, thioether, carbonyl and unsubstituted or substitute methyl wherein the group $R_2$ is selected from a group consisting of H, methyl, ethyl and carboxylalkyl; and e) the lanthanide ion is europium(III), terbium(III), dysprosium(III) or samarium(III).

According to another aspect the present invention provides a detectable molecule comprising a biospecific binding reactant attached to a luminescent lanthanide chelate comprising a lanthanide ion and a chelating ligand of the formula (I)

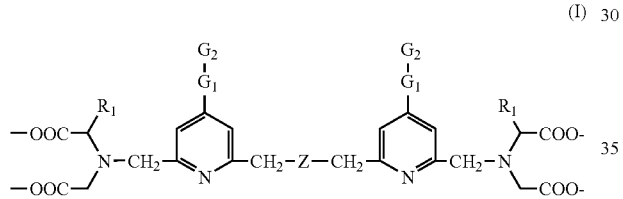

wherein, a) $R_1$ is selected from the group consisting of H, —COOH, —COO⁻, —CH₂COOH and —CH₂COO⁻;

b) $G_1$ is a group consisting of one or two moieties, each moiety being selected from the group consisting of ethynediyl, ethenylene, phenylene, biphenylene, naphthylene, pyridylene, pyrazinylene, pyrimidinylene, pyridazinylene, furylene, thienylene, pyrrolylene, imidazolylene, pyrazolylene, thiazolylene, isothiazolylene, oxazolylene, isoxazolylene, fyrazanylene, 1,2,4-triazol-3,5-ylene and oxadiazolylene;

c) $G_2$ for coupling to a biospecific binding reactant is selected from the group consisting of thiourea, aminoacetamide, amide, aliphatic thioether, disulfide or 6-substituted-1,3,5-tiazine-2,4-diamine;

d) Z is selected from the group consisting of carboxyalkyl amine, ether, thioether, carbonyl and unsubstituted or substitute methyl wherein group $R_2$ is selected from the group consisting of H, methyl, ethyl and carboxylalkyl; and e) the lanthanide ion is europium(III), terbium(III), dysprosium(III) or samarium(III).

According to yet another aspect the present invention provides an improved labeling method of a biospecific binging reactant. The method uses the luminescent lanthanide chelate label of the present invention.

DETAILED DESCRIPTION OF THE INVENTION

Figure 1:
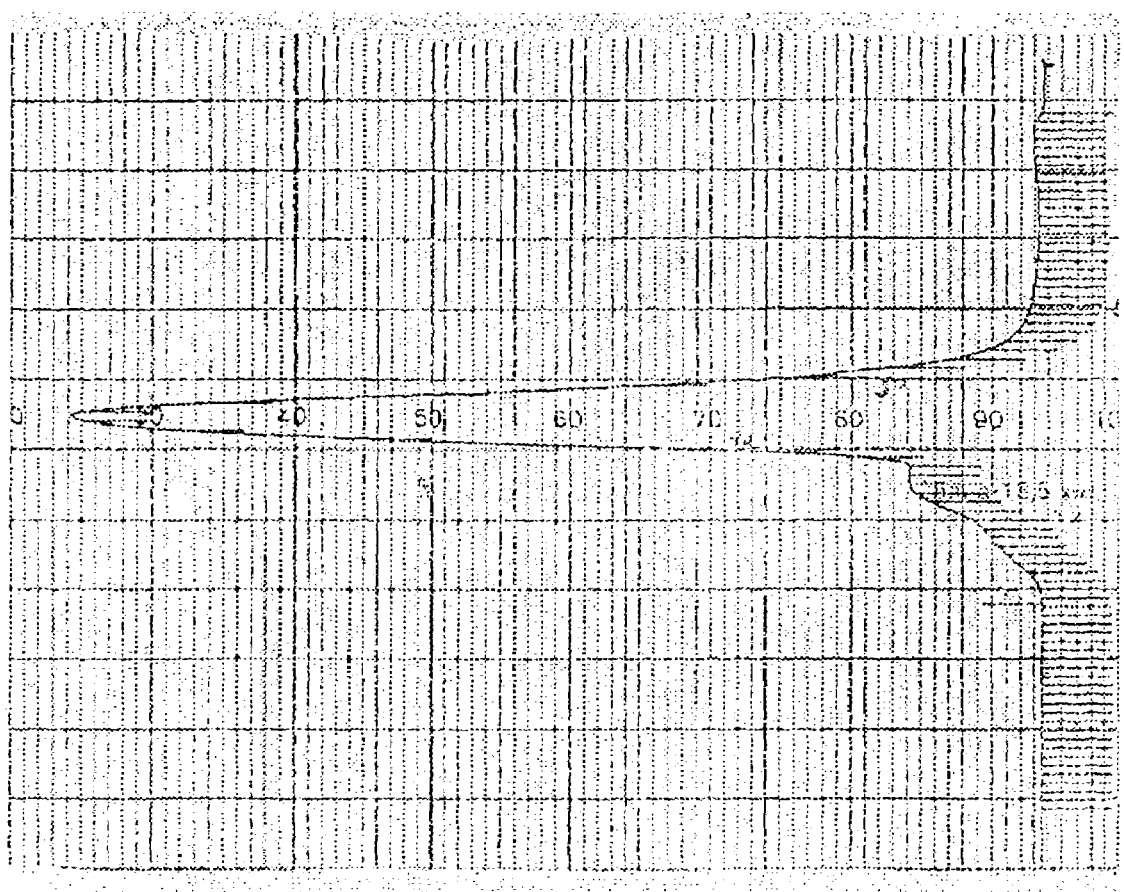
FIG. 1 illustrates a purification profile of a protein labeled with a europium(III) chelate of the present invention.

According to the present invention providing a nine- or ten-dentate lanthanide chelate with two binding groups decreases aqueous quenching even compared to prior art seven to nine-dentate chelates. A non-radiative deactivation process of the triplet state caused by label rotation is prevented, and a more luminescent lanthanide chelate is made possible, and moreover at the same time, all other important features of labels and labeled biomolecules can be retained without any additional forming of aggregates and purification problems.

The aim of the present invention is to provide means to obtain improved lanthanide chelate labels to be used in specific bioaffinity based binding assays, such as immunoassays (both heterogeneous and homogenous assays), DNA hybridization assays, receptor binding assays, immunocytochemical or immunohistochemical assays utilizing fluorometric or time-resolved fluorometric determination of the specific luminescence.

The chelates of this invention combine several important features in a single label, such as 1. high absorptivity at suitable wavelength, preferable over 300 nm,
2. several separate UV absorbing parts (chromophors) in the same ligand structure, preferable two chromophors,
3. effective energy transfer from the UV absorbing part (triplet sensitizer) to the lanthanide ion,
4. a strongly chelating part to create a) thermodynamic stability required for storing the labeled reactants for extended periods of time, and b) high kinetic stability to allow the use of reactants in conditions where competing metal ions or chelating agents may be present,
5. a chelating part forming as complete a protection of the chelated ion as possible, preferable a nine-dentate ligand, and more preferable a ten-dentate ligand,
6. a functional group allowing effective coupling of the chelate to be used as a binding reactant (e.g. antibody) without destroying its binding properties and decreasing the luminescence properties of the label, preferable two said functional groups preventing label rotation after coupling to a biospecific binging reactant.

In addition, the chelate has to be highly hydrophilic and possess low nonspecific binding affinity to proteins or surfaces used in the analysis.

The present invention provides a luminescent lanthanide chelate comprising a lanthanide ion and a chelating ligand of the formula (I)

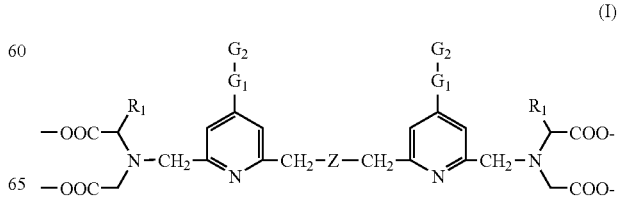

wherein,
a) $R_1$ is selected from the group consisting of H, —COOH, —COO⁻, —CH$_2$COOH and —CH$_2$COO⁻;
b) $G_1$ is a group consisting of one or two moieties each moiety being selected from the group consisting of ethynediyl (—C≡C—), ethenylene (—CH=CH—), phenylene, biphenylene, naphthylene, pyridylene, pyrazinylene, pyrimidinylene, pyridazinylene, furylene, thienylene, pyrrolylene, imidazolylene, pyrazolylene, thiazolylene, isothiazolylene, oxazolylene, isoxazolylene, fyrazanylene, 1,2,4-triazol-3,5-ylene and oxadiazolylene;
c) $G_2$ for coupling to a biospecific binding reactant is selected from the group containing amino, aminooxy, carbonyl, aldehyde or mercapto groups or an activated form made of them such as isocyanato, isothiocyanato, diazonium, bromoacetamido, iodoacetamido, reactive esters, pyridyl-2-dithio or 6-substituted 4-chloro-1,3,5-triazin-2-ylamino;
d) Z is selected from the group consisting of carboxyalkyl amine {—N[(CH$_2$)$_n$COOH]— or —N[(CH$_2$)$_n$COO⁻]— and n=1, 2, 3, 4, 5 or 6}, ether (—O—), thioether (—S—), carbonyl (—CO—) and unsubstituted or substitute methyl (—CR$_2$—) wherein the group $R_2$ is selected from a group consisting of H, methyl, ethyl and carboxylalkyl [—(CH$_2$)$_n$COOH or —CH$_2$)$_n$COO⁻ and n=1, 2, 3, 4, 5 or 6]; and
e) the lanthanide ion is europium(III), terbium(III), dysprosium(III) or samarium(III).

The present invention also provides a detectable molecule comprising a biospecific binding reactant attached to a luminescent lanthanide chelate comprising a lanthanide ion and a chelating ligand of formula (I)

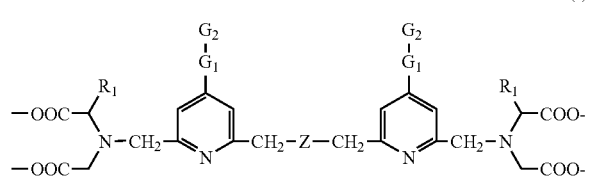

(I)

wherein,
a) $R_1$ is selected from the group consisting of H, —COOH, —COO⁻, —CH$_2$COOH and —CH$_2$COO⁻;
b) $G_1$ is a group consisting of one or two moieties, each moiety being selected from the group consisting of ethynediyl (—C≡C—), ethenylene (—CH=CH—), phenylene, biphenylene, naphthylene, pyridylene, pyrazinylene, pyrimidinylene, pyridazinylene, furylene, thienylene, pyrrolylene, imidazolylene, pyrazolylene, thiazolylene, isothiazolylene, oxazolylene, isoxazolylene, fyrazanylene, 1,2,4-triazol-3,5-ylene and oxadiazolylene;
c) $G_2$ for coupling to a biospecific binding reactant is selected from the group consisting of thiourea (—NH—CS—NH—), aminoacetamide (—NH—CO—CH$_2$—NH—), amide (—NH—CO—, —CO—NH—, —NCH$_3$—CO— and —CO—NCH$_3$—), aliphatic thioether (—S—), disulfide (—S—S—) or 6-substituted-1,3,5-triazine-2,4-diamine;
d) Z is selected from the group consisting of carboxyalkyl amine {—N[(CH$_2$)$_n$COOH]— or —N[(CH$_2$)$_n$COO⁻]— and n=1, 2, 3, 4, 5 or 6}, ether (—O—), thioether (—S—), carbonyl (—CO—) and unsubstituted or substitute methyl (—CR$_2$—) wherein group $R_2$ is selected from the group consisting of H, methyl, ethyl and carboxylalkyl [—(CH$_2$)$_n$COOH or —(CH$_2$)$_n$COO⁻ and n=1, 2, 3, 4, 5 or 6]; and
e) the lanthanide ion is europium(III), terbium(III), dysprosium(III) or samarium(III).

This invention further relates to the use of a detectable molecule as defined above in biospecific binding assays.

The biospecific binding reactant is selected from a group consisting of an antibody, an antigen, a receptor ligand, a specific binding protein or peptide, and a DNA- or RNA-probe.

The substituents in 6-substituted-1,3,5-triazine-2,4-diamine and 6-substituted 4-chloro-1,3,5-triazin-2-ylamino can be selected from the group consisting of H, halogen, alkoxy, aryloxy, amino, lower alkyl, substituted amino and thioesters, and preferable selected from the group consisting of chloro, fluoro, ethoxy, 2-methoxyethoxy, 2-cyanoethoxy, 2,2,2-trifluoroethoxy, thiophenoxy and ethoxycarbonylyhiomethoxy.

The term "luminescent" shall in this invention be understood to mean "photoluminescent" as already stated above.

According to a preferable embodiment of the invention the lanthanide ion is either europium(III) or terbium(III).

The invention is further exemplified by the following examples demonstrating the effect of prevented label rotation by two binding groups together with a ten-dentate chelate structure on luminescence intensity and decay times.

The structures and the synthetic route employed in the experimental part are shown in reaction scheme 1a and 1b. The schemes illustrate the synthesis of compound 5 exemplified by examples 1 to 5. Scheme 2 illustrates the structures of reference label compounds 6 and 7. Compound 6 is a seven-dentate europium(III) label. Compound 7 is a nine-dentate europium(III) label with two separate chromophors and one binding group. The purification profile, shown in FIG. 1, of a label protein according to the invention demonstrates low aggregation and the absence of labeling chelate, and thus shows that the protein labeled with a compound of the present invention, i.e. by using several reactive binding groups in a label molecule, does surprisingly not cause purification problems nor decrease yield of labeled material.

EXAMPLES

Example 1

The synthesis of tetra(tert-butyl) 2,2',2'',2'''-{[(ethoxycarbonyl)methylimino]bis(methylene)bis(4-bromopyridine-6,2-diyl)bis(methylenenitrilo)}tetrakis(acetate) (1)

Di(tert-butyl) 2,2'-{[4-bromo-6-(bromomethyl)pyridin-2-yl]methylenenitrilo}bis-(acetate) (2.04 g, 4.014 mmol) was dissolved in dry acetonitrile (40 ml). To the mixture was added ethyl glycinate hydrochloride (0.28 g, 2.006 mmol) and diisopropylethylamine (2.8 ml, 16.07 mmol). After stirring for 4 hours at 48° C., the mixture was evaporated. The residue was dissolved in chloroform (120 ml) and washed twice with water (2×30 ml), dried with sodium sulfate and evaporated. The product was purified with flash chromatography (silica, first 20% ethyl acetate in petroleum ether and finally 50%) The yield was 0.82 g (43%). $^1$H NMR(CDCl$_3$, 400 MHz): 7.75 (2H, s), 7.63 (2H, s), 4.1 (2H, q, J=7.04 Hz), 4.00 (4H, s), 3.93 (4H, s), 3.37 (10H, s), 1.46 (36H, s), 1.29 (3H, t, J=7.04 Hz).

Example 2

The synthesis of tetra(tert-butyl) 2,2',2",2'''-{[(ethoxycarbonyl)methylimino]bis-(methylene)bis{[4-[(4-amino)phenyl]ethynyl]pyridine-6,2-diyl}bis(methylenenitrilo)}tetrakis(acetate) (2)

A mixture of compound 1 (0.3 g, 0.313 mmol), bis(triphenylphosphine)palladium(II)chloride (8.8 mg, 0.0126 mmol) and copper(I) iodide (4.8 mg, 0.0252 mmol) in dry triethylamine (4 ml) and tetrahydrofuran (4 ml) was deaerated with argon. [(4-Amino)phenyl]acetylene (88 mg, 0.751 mmol) was added to the mixture and the reaction was stirred overnight at 51° C., after which it was filtered and the filtrate evaporated. The residue was dissolved in chloroform (45 ml) and washed twice with water (2×15 ml), dried with sodium sulfate and evaporated. The product was purified with flash chromatography (silica, first from 1% to 10% methanol in dichloromethane, and finally methanol) The yield was 0.24 g (75%). $^1$H NMR(CDCl$_3$, 400 MHz): 7.56 (2H, s), 7.53 (2H, s) 7.32 (4H, d, J=8.56 Hz), 6.58 (4H, d, J=8.56 Hz), 4.17 (2H, q, J=7.2 Hz)), 4.01 (4H, s), 3.97 (4H, s), 3.48(10H, s), 1.46 (36H, s), 1.28 (3H, t, J=7.2 Hz).

Example 3

The synthesis of 2,2',2",2'''-{[(ethoxycarbonyl)methylimino]bis(methylene)-bis{[4-[(4-amino)phenyl]ethynyl]pyridine-6,2-diyl}bis(methylenenitrilo)}tetrakis-(acetic acid) (3)

A solution of compound 2 (0.1 g, 0.097 mmol) in trifluoroacetic acid (2 ml) was stirred for 2 hours at room temperature. After evaporation without heating, the mixture was triturated with diethylether (10 ml) and filtered. Filtration left a pure product. The yield was 0.13 g. $^1$H NMR(DMSO, 400 MHz): 7.32 (4H, s), 7.11 (4H, d, J=8.3 Hz), 6.42 (4H, d, J=8.3 Hz), 3.94 (2H, q, J=7.1 Hz), 3.82 (8H, s), 3.37 (10H, s), 1.06 (3H, t, J=7.1 Hz).

Example 4

The synthesis of {2,2',2",2'''-{[(carboxymethyl)imino]bis(methylene)-bis{[4-[(4-amino)phenyl]ethynyl]pyridine-6,2-diyl}bis(methylenenitrilo)}tetrakis(acetato)}-europium(III) (4)

A mixture of compound 3 (180 mg, 0.164 mmol), 0.5 M potassium hydroxide in ethanol (10 ml) and water (4.5 ml) was stirred for 2 hours at room temperature. After evaporation, the residue was dissolved in water (4.5 ml) and the pH was adjusted to 6.5 with 6 M hydrochloride. Europium (III) chloride hexahydrate (66 mg, 0.18 mmol) in water (1.9 ml) was added within 10 minutes and the pH maintained at 6.5 with solid sodium carbonate. After stirring the reaction for 1 hour, the pH was raised to 8.5 with 1 M sodium hydroxide and the precipitate removed by centrifugation. The filtrate was the treated with acetone, and the product was collected by centrifugation and washed with acetone. The product was used in next step without purification. The yield was 300 mg. UV(water): 339, 257 and 247 nm. ESI-TOF-MS mass for $C_{40}H_{34}EuN_7O_{10}M^-$ (monoisotopic): calculated 924.70, found 924.04.

Example 5

The synthesis of {2,2',2",2'''-{[(carboxymethyl)imino]bis(methylene)-bis{[4-[(4-isothiocyanato)phenyl]ethynyl]pyridine-6,2-diyl}bis(methylenenitro)}tetrakis-(acetato)}europium(III) (5)

The compound 4 (360 mg, 0.374 mmol) in water (6.0 ml) was added slowly to a mixture of thiophosgene (230 µl, 3.027 mmol), sodium hydrogencarbonate (315 mg, 3,750 mmol) and chloroform (6.0 ml). After stirring for 1 hour, the water phase was washed twice with chloroform (2×12 ml). The pH of aqueous solution was adjusted to 7.0 with 1 M acetic acid and added acetone to water phase. The product was collected by centrifugation and washed with acetone. The yield was 490 mg. UV(water): 333, 319 and 228 nm. ESI-TOF-MS mass for $C_{42}H_{30}EuN_7O_{10}S_2M^-$ (monoisotopic): calculated 1008.83, found 1007.96.

Example 6

Coupling of the chelate 5,7-dentate and 9-dentate Eu-chelates (6 and 7 in Scheme 2) to protein Labeling was performed in 10 mM borate buffer, pH 8.6–9.0 using 15- (for the chelate 5) 50- (for the chelate 6) and 150-fold (for the chelate 7) molar excesses. Reactions were normally carried out overnight at +4° C. or at room temperature. Labeled antibodies were purified on Superfex 200 HR 10/30 or Superdex 200 HiLoad 26/60 gel filtration columns (Pharnacia Biotech) using Tris-saline-azide (6.1 g/L Tris, 9.0 g/L NaCl, and 0.5 g/L NaN$_3$), pH 7.75 as an elution buffer. The fractions containing the antibody were pooled and the europium concentrations measured against a europium calibrator (Innotrac Diagnostics Oy). The purified antibody conjugate and the labeling ratio (chelates per protein) were quantified by calculating the protein yield or by measuring the absorbance at 280 nm and subtracting the absorption caused by the added chelate.

Example 7

The Luminescence Measurements of the Chelate-labelled Antibodies

The luminescence parameters for the Eu labeled antibodies were measured in buffer containing 5 mM Hepes, 2.1 g/L NaCl, 0.1 mM EDTA, 0.055 g/L Tween20 and 1 g/L Germall II, pH 7.75. The excitation and emission spectra, luminescence intensities and decay times were measured using a LS55 Luminescence Spectrometer (PerkinElmer Instruments), while the molar extinction coefficients (absorbance) were determined with a UV-2100 Spectrophotometer (Shimadzu). Additionally, decay times were also measured from antibody bound to solid phase after buffer aspirating and drying of the wells. The solid phase determinations were performed using Cary Eclipse Fluorescence Spectrophotometer (Varian). The luminescence measurements were standardized using 0.1 µM Eu(III) in Wallac Delfia enhancement soln. (molar absortivity 37600, quantum yield 70% and luminescence yield 26320). The emission intensities were measured using the most intense emission line at ca. 613 nm.

TABLE 1

The emission maxima ($\lambda_{exc}$), luminescence decay times ($\tau$) and luminescence yields ($\epsilon \cdot \Phi$) of Eu (III) chelates 5, 6 and 7 in protein in Hepes buffer, pH 7.75.

| Chelate | $\lambda_{exc}$[nm] | $\tau$[μs] | $\epsilon \cdot \Phi$ |
|---|---|---|---|
| 5 | 328 | 1120 | 8025 |
| 6 | 329 | 390 | 1337 |
| 7 | 325 | 1000 | 4787 |

TABLE 2

Decay times ($\tau$) of EU (III) chelates 5, 6 and 7 coupled in protein in various environments.

| Chelate | $\tau$[μs]/Hepes | $\tau$[μs]/wet surface | $\tau$[μs]/dry surface |
|---|---|---|---|
| 5 | 1120 | 1130 | 1290 |
| 6 | 390 | 490 | 1150 |
| 7 | 1000 | 1000 | 990 |

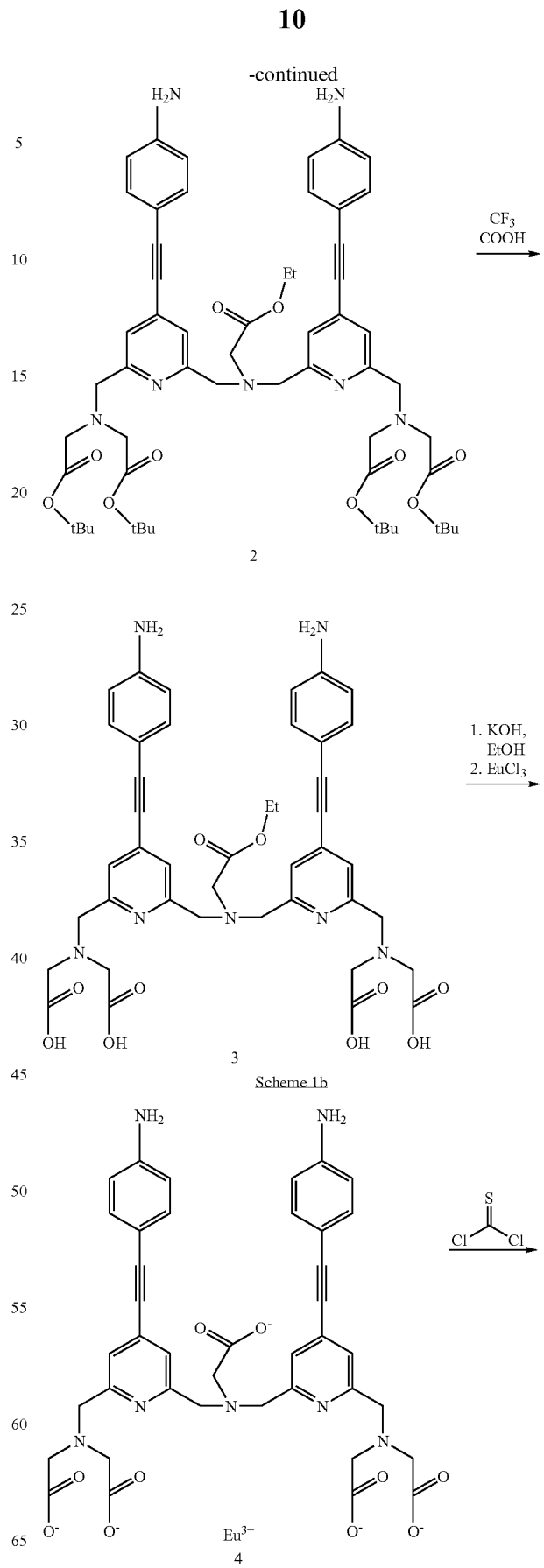

-continued

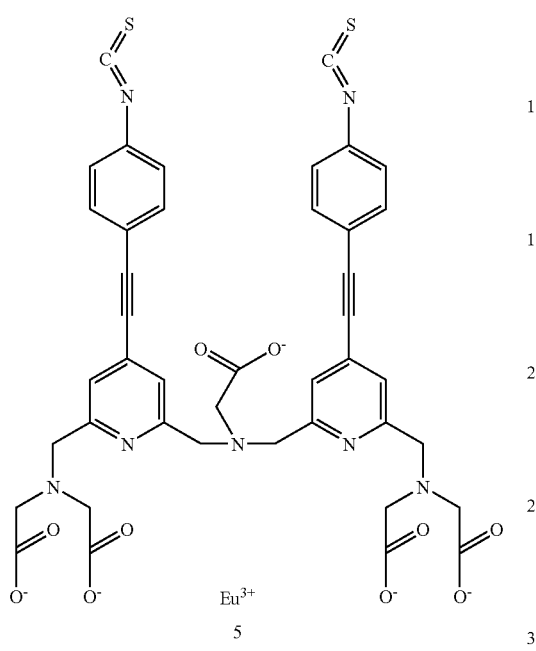

5

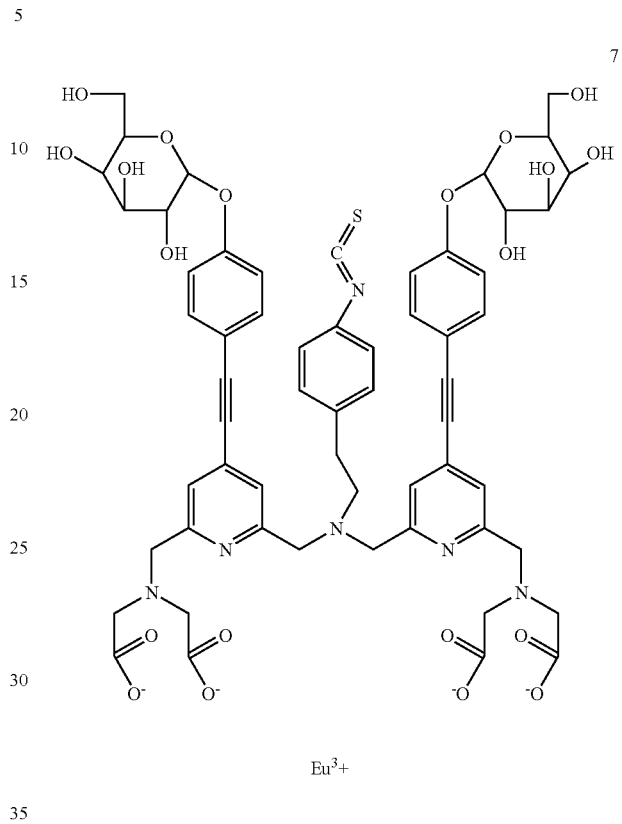

7

Scheme 2

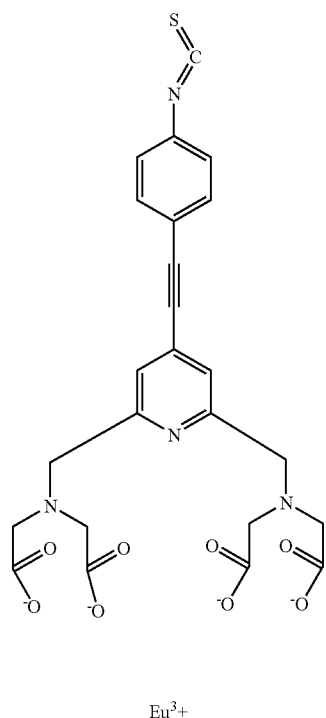

6

Eu³⁺

The invention claimed is:

1. A luminescent lanthanide chelate comprising a lanthanide ion and a chelating ligand of formula (I)

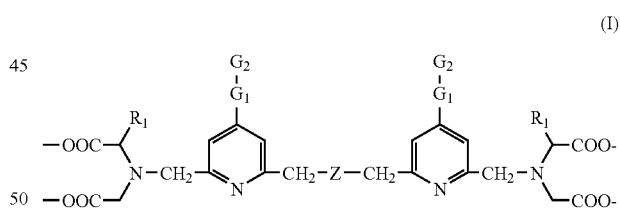

(I)

wherein

R₁ is selected from the group consisting of H, —COOH, —COO⁻, —CH₂COOH and —CH₂COO⁻;

G₁ is a group consisting of one or two moieties, each moiety being selected from the group consisting of ethynediyl (—C≡C—), ethenylene (—CH═CH—), phenylene, biphenylene, naphthylene, pyridylene, pyrazinylene, pyrunidinylene, pyridazinylene, furylene, thienylene, pyrrolylene, imidazolylene, pyrazolylene, thiazolylene, isothiazolylene, oxazolylene, isoxazolylene, furazanylene, 1,2,4-triazol-3,5-ylene and oxadiazolylene;

G₂ is a group capable of being coupled to a biospecific binding reactant and is selected from the group consisting of amino, aminooxy, carboxyl, aldehyde or mercapto groups and activated forms made of them;

Z is selected from the group consisting of carboxyalkyl amine {—N[(CH$_2$)$_n$COOH] or —N[(CH$_2$)$_n$COO$^-$]— and n=1, 2, 3, 4. 5, or 6}, ether (—O—), thioether (—S—), carbonyl (—CO—) and unsubstituted or substituted methyl (—CR$_2$—) wherein group R$_2$ is selected from the group consisting of H, methyl, ethyl and carboxyalkyl{—CH$_2$)$_n$COOH or —(CH$_2$)$_n$COO$^-$ and n=1, 2, 3, 4. 5, or 6; and the lanthanide ion is a member selected from the group consisting of europium (III), terbium (III), dysprosium (III) and samarium(III).

2. The lanthanide chelate according to claim 1 wherein G$_2$ is said activated form selected form the group consisting of isocyanato, isothiocyanato, diazonium, bromoacetamido, iodoacetamido, reactive esters, pyridyl-2-dithio and 6-substituted 4-chloro-1,3,5-triazin-2-ylamino.

3. The lanthanide chelate according to claim 1 wherein the chelating ligand is {2,2',2'',2' ''-{[(carboxymethyl)imino]bis(methylene)-bis{[(4-[(4-isothiocyanato)-phenyl]ethynyl]pyridine-6,2-diyl}bis(methylenenitrilo)}tetrakis(acetato)}-europium(III).

4. A detectable molecule which comprises a biospecific binding reactant attached to a luminescent lanthanide chelate comprising a lanthanide ion and a chelating ligand of formula (II)

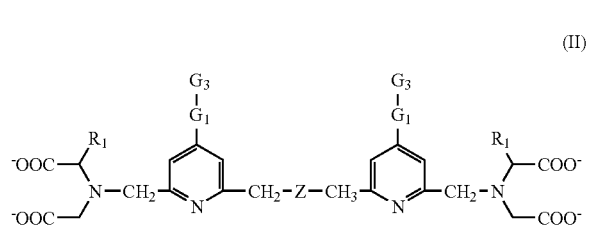

(II)

wherein
R$_1$ is selected from the group consisting of H, —COOH, —COO$^-$, —CH$_2$COOH and —CH$_2$COO$^-$;
G$_1$ is a group consisting of one or two moieties, each moiety being selected from the group consisting of ethynediyl (—C≡C—), ethenylene (—CH═CH—), phenylene, biphenylene, naphthylene, pyridylene, pyrazinylene, pyrimidinylene, pyridazinylene, furylene, thienylene, pyrrolylene, imidazolylene, pyrazolylene, thiazolylene, isothiazolylene, oxazolylene, isoxazolylene, furazanylene, 1,2,4-triazol-3,5-ylene and oxadiazolylene;
G$_3$ is a group coupled to said biospecific binding reactant and is selected from the group consisting of thiourea (—NH—CS—NH—), aminoacetamide (—NH—CO—CH$_2$—NH—), amide (—NH—CO—, —CO—NH—, —NCH$_3$—CO— and —CO—NCH$_3$—), aliphatic thioether (—S—), disulfide (—S—S—) and 6-substituted-,1,3,5,-triazine-2,4-diamine;
Z is selected from the group consisting of carboxyalkyl amine {—N[(CH$_2$)$_n$COOH]— or —N[(CH$_2$)$_n$COO$^-$]— wherein n is 1, 2, 3, 4, 5, or 6}, ether (—O—), thioether (—S—), carbonyl (—CO—) and unsubstituted or substituted methyl (—CR$_2$—) wherein group R$_2$ is selected from the group consisting of H, methyl, ethyl and carboxyalkyl [—(CH$_2$)$_n$COOH]— or —{(CH$_2$)$_n$COO$^-$]— wherein n is 1, 2, 3, 4. 5, or 6}; and the lanthanide ion is a member selected from the group consisting of europium (III), terbium (III), dysprosium (III) and samarium(III).

5. The detectable molecule according to claim 4, wherein the biospecific binding reactant is selected from the group consisting of an antibody, an antigen, a receptor ligand, a specific binding protein, a DNA probe and an RNA probe.

6. The detectable molecule according to claim 4, wherein the lanthanide chelate attached to a biospecific binding reactant is {2,2',2'',2'''-{[(carboxymethyl)-imino]bis(methylene)-bis{[4-[(4-thioureylene)phenyl]ethynyl]pyridine-6, 2-diyl}bis(methylenenitrilo)tetrakis-(acetato)}-europium (III).

7. A method of performing a biospecific binding assay, comprising
labelling an analyte with a detectable molecule comprising a biospecific binding reactant attached to a luminescent lanthanide chelate, thereby forming a labelled analyte;
exciting said labelled analyte with radiation having an excitation wavelength, thereby forming an excited labelled analyte; and
detecting emission radiation emitted from said excited labelled analyte,
wherein said luminescent lanthanide chelate comprises a lanthanide ion and a chelating ligand of formula (II)

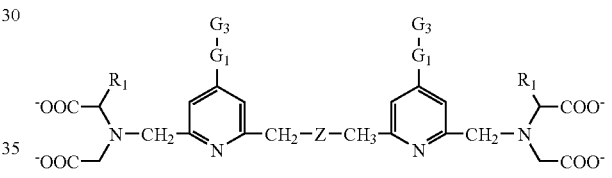

(II)

wherein
R$_1$ is selected from the group consisting of H, —COOH, —COO$^-$, —CH$_2$COOH and —CH$_2$COO$^-$;
G$_1$ is a group consisting of one or two moieties, each moiety being selected from the group consisting of ethynediyl (—C≡C—), ethenylene (—CH═CH—), phenylene, biphenylene, naphthylene, pyridylene, pyrazinylene, pyrimidinylene, pyridazinylene, furylene, thienylene, pyrrolylene, imidazolylene, pyrazolylene, thiazolylene, isothiazolylene, oxazolylene, isoxazolylene, furazanylene, 1,2,4 triazol-3,5-ylene and oxadiazolylene;
G$_3$ is a group coupled to said biospecific binding reactant and is selected from the group consisting of thiourea (—NH—CS—NH—), aminoacetamide (—NH—CO—CH$_2$—NH—), amide (—NH—CO—, —CO—NH—, —NCH$_3$—CO— and —CO—NCH$_3$—), aliphatic thioether (—S—), disulfide (—S—S—) and 6-substituted-1,3,5,-triazine-2,4-diamine;
Z is selected from the group consisting of carboxyalkyl amine {—N[(CH$_2$)$_n$COOH]— or —N[(CH$_2$)$_n$COO$^-$] wherein n is 1, 2, 3, 4, 5, or 6}, ether (—O—), thioether (—S—), carbonyl (—CO—) and unsubstituted or substituted methyl (—CR$_2$—) wherein group R$_2$ is selected from the group consisting of H, methyl, ethyl and carboxyalkyl [—(CH$_2$)$_n$COOH]— or —[(CH$_2$)$_n$COO$^-$]— wherein n is 1, 2, 3, 4, 5, or 6; and
the lanthanide ion is a member selected from the group consisting of europium (III), terbium (III), dysprosium (III) and samarium(III).

8. The method according to claim 7, wherein the biospecific binding reactant is selected from the group consisting of an antibody, an antigen, a receptor ligand, a specific binding protein, a DNA probe and an RNA probe.

9. The method according to claim 7, wherein the lanthanide chelate attached to a biospecific binding reactant is {2,2',2'',2'''-{[(carboxymethyl)imino]bis(methylene)-bis{[4-[(4-thioureylene)-phenyl]ethynyl]pyridine-6,2-diyl}bis(methylenenitrilo)}tetrakis(acetato)}-europium(III).

* * * * *

UNITED STATES PATENT AND TRADEMARK OFFICE
CERTIFICATE OF CORRECTION

PATENT NO.      : 7,018,851 B2
APPLICATION NO. : 10/365637
DATED           : March 28, 2006
INVENTOR(S)     : Harri Takalo and Jaana Rosenberg It is certified that error appears in the above-identified patent and that said Letters Patent is hereby corrected as shown below:

Col. 11, below line 65 ( after the lower formula), insert -- 6 --; and
Col. 12, line 35 (after the formula), insert -- 7 -- .

Claim 1, Col. 12, line 60, change "pyrunidinylene," to -- pyrimidinylene, --.

Signed and Sealed this

Twentieth Day of February, 2007

JON W. DUDAS
*Director of the United States Patent and Trademark Office*